US008968267B2

(12) United States Patent
Nelson et al.

(10) Patent No.: US 8,968,267 B2
(45) Date of Patent: Mar. 3, 2015

(54) METHODS AND SYSTEMS FOR HANDLING OR DELIVERING MATERIALS FOR NATURAL ORIFICE SURGERY

(75) Inventors: Carl A Nelson, Lincoln, NE (US); Jeff Midday, Lake Zurich, IL (US); Dimitry Oleynikov, Lincoln, NE (US); Alan Goyzueta, Longview, TX (US)

(73) Assignee: Board of Regents of the University of Nebraska, Lincoln, NE (US)

( * ) Notice: Subject to any disclaimer, the term of this patent is extended or adjusted under 35 U.S.C. 154(b) by 431 days.

(21) Appl. No.: 13/204,231

(22) Filed: Aug. 5, 2011

(65) Prior Publication Data

US 2012/0035582 A1 Feb. 9, 2012

Related U.S. Application Data

(60) Provisional application No. 61/371,361, filed on Aug. 6, 2010.

(51) Int. Cl.
*A61M 31/00* (2006.01)
*A61B 17/00* (2006.01)
*A61B 17/22* (2006.01)
*A61B 17/50* (2006.01)
*A61B 17/221* (2006.01)
(Continued)

(52) U.S. Cl.
CPC ..... *A61B 17/00234* (2013.01); *A61B 17/22031* (2013.01); *A61B 17/50* (2013.01); *A61B 17/221* (2013.01); *A61B 2017/00287* (2013.01); *A61B 2017/00685* (2013.01); *A61B 2017/22034* (2013.01); *A61B 2017/320064* (2013.01); *A61B 2017/320775* (2013.01)
USPC ............................ 604/500; 604/264; 604/131

(58) Field of Classification Search
CPC .................. A61B 17/00234; A61B 17/22031; A61B 2017/00685; A61B 2017/22034; A61B 2017/320064; A61B 2017/320775
USPC ......................................... 604/500, 131, 264
See application file for complete search history.

(56) References Cited

U.S. PATENT DOCUMENTS 3,870,264 A    3/1975   Robinson
3,989,952 A    11/1976  Hohmann
(Continued)

FOREIGN PATENT DOCUMENTS

EP    2286756 A1    2/2011
JP    2004144533    5/1990
(Continued)

OTHER PUBLICATIONS

Patronik et al., "Crawling on the Heart: A Mobile Robotic Device for Minimally Invasive Cardiac Interventions," MICCAI, 2004, pp. 9-16.
(Continued)

*Primary Examiner* — Edelmira Bosques
(74) *Attorney, Agent, or Firm* — Davis, Brown, Koehn, Shors & Roberts, P.C.; Sean D. Solberg

(57) ABSTRACT

The embodiments disclosed herein relate to various medical systems, including systems that can be used in conjunction with medical devices used in endoscopic surgery. Certain embodiments include various material handling devices that can transport materials between the inside and the outside of an endoscopic surgery patient.

18 Claims, 8 Drawing Sheets

(51) Int. Cl.
*A61B 17/32* (2006.01)
*A61B 17/3207* (2006.01)

(56) References Cited

U.S. PATENT DOCUMENTS

| | | | |
|---|---|---|---|
| 4,246,661 A | 1/1981 | Pinson | |
| 4,258,716 A | 3/1981 | Sutherland | |
| 4,278,077 A | 7/1981 | Mizumoto | |
| 4,538,594 A | 9/1985 | Boebel et al. | |
| 4,568,311 A | 2/1986 | Miyake | |
| 4,623,183 A | 11/1986 | Amori | |
| 4,736,645 A | 4/1988 | Zimmer | |
| 4,771,652 A | 9/1988 | Zimmer | |
| 4,852,391 A | 8/1989 | Ruch et al. | |
| 4,896,015 A | 1/1990 | Taboada et al. | |
| 4,897,014 A | 1/1990 | Tietze | |
| 4,922,755 A | 5/1990 | Oshiro et al. | |
| 4,990,050 A | 2/1991 | Tsuge et al. | |
| 5,019,968 A | 5/1991 | Wang et al. | |
| 5,108,140 A | 4/1992 | Bartholet | |
| 5,172,639 A | 12/1992 | Wiesman et al. | |
| 5,176,649 A | 1/1993 | Wakabayashi | |
| 5,178,032 A | 1/1993 | Zona et al. | |
| 5,187,032 A | 2/1993 | Sasaki et al. | |
| 5,187,796 A | 2/1993 | Wang et al. | |
| 5,195,388 A | 3/1993 | Zona et al. | |
| 5,201,325 A | 4/1993 | McEwen et al. | |
| 5,217,003 A | 6/1993 | Wilk | |
| 5,263,382 A | 11/1993 | Brooks et al. | |
| 5,271,384 A | 12/1993 | McEwen et al. | |
| 5,284,096 A | 2/1994 | Pelrine et al. | |
| 5,297,443 A | 3/1994 | Wentz | |
| 5,297,536 A | 3/1994 | Wilk | |
| 5,304,899 A | 4/1994 | Sasaki et al. | |
| 5,307,447 A | 4/1994 | Asano et al. | |
| 5,353,807 A | 10/1994 | DeMarco | |
| 5,363,935 A | 11/1994 | Schempf et al. | |
| 5,382,885 A | 1/1995 | Salcudean et al. | |
| 5,388,528 A | 2/1995 | Pelrine et al. | |
| 5,436,542 A | 7/1995 | Petelin et al. | |
| 5,441,494 A | 8/1995 | Ortiz | |
| 5,458,131 A | 10/1995 | Wilk | |
| 5,458,583 A | 10/1995 | McNeely et al. | |
| 5,458,598 A | 10/1995 | Feinberg et al. | |
| 5,471,515 A | 11/1995 | Fossum et al. | |
| 5,515,478 A | 5/1996 | Wang | |
| 5,524,180 A | 6/1996 | Wang et al. | |
| 5,553,198 A | 9/1996 | Wang et al. | |
| 5,562,448 A | 10/1996 | Mushabac | |
| 5,588,442 A | 12/1996 | Scovil et al. | |
| 5,620,417 A | 4/1997 | Jang et al. | |
| 5,623,582 A | 4/1997 | Rosenberg | |
| 5,624,398 A | 4/1997 | Smith et al. | |
| 5,632,761 A | 5/1997 | Smith et al. | |
| 5,645,520 A | 7/1997 | Nakamura et al. | |
| 5,657,429 A | 8/1997 | Wang et al. | |
| 5,657,584 A | 8/1997 | Hamlin | |
| 5,674,030 A | 10/1997 | Sigel | |
| 5,728,599 A | 3/1998 | Rosteker et al. | |
| 5,736,821 A | 4/1998 | Suyama et al. | |
| 5,754,741 A | 5/1998 | Wang et al. | |
| 5,762,458 A | 6/1998 | Wang et al. | |
| 5,769,640 A | 6/1998 | Jacobus et al. | |
| 5,791,231 A | 8/1998 | Cohn et al. | |
| 5,792,135 A | 8/1998 | Madhani et al. | |
| 5,797,900 A | 8/1998 | Madhani et al. | |
| 5,807,377 A | 9/1998 | Madhani et al. | |
| 5,815,640 A | 9/1998 | Wang et al. | |
| 5,825,982 A | 10/1998 | Wright et al. | |
| 5,841,950 A | 11/1998 | Wang et al. | |
| 5,845,646 A | 12/1998 | Lemelson | |
| 5,855,583 A | 1/1999 | Wang et al. | |
| 5,860,987 A * | 1/1999 | Ratcliff et al. | 606/113 |
| 5,876,325 A | 3/1999 | Mizuno et al. | |
| 5,878,193 A | 3/1999 | Wang et al. | |
| 5,878,783 A | 3/1999 | Smart | |
| 5,895,417 A | 4/1999 | Pomeranz et al. | |
| 5,906,591 A | 5/1999 | Dario et al. | |
| 5,907,664 A | 5/1999 | Wang et al. | |
| 5,911,036 A | 6/1999 | Wright et al. | |
| 5,971,976 A | 10/1999 | Wang et al. | |
| 6,001,108 A | 12/1999 | Wang et al. | |
| 6,007,550 A | 12/1999 | Wang et al. | |
| 6,030,365 A | 2/2000 | Laufer | |
| 6,031,371 A | 2/2000 | Smart | |
| 6,058,323 A | 5/2000 | Lemelson | |
| 6,063,095 A | 5/2000 | Wang et al. | |
| 6,066,090 A | 5/2000 | Yoon | |
| 6,102,850 A | 8/2000 | Wang et al. | |
| 6,107,795 A | 8/2000 | Smart | |
| 6,132,368 A | 10/2000 | Cooper | |
| 6,132,441 A | 10/2000 | Grace | |
| 6,156,006 A | 12/2000 | Brosens et al. | |
| 6,159,146 A | 12/2000 | El Gazayerli | |
| 6,162,171 A | 12/2000 | Ng et al. | |
| 6,193,692 B1 * | 2/2001 | Harris et al. | 604/164.02 |
| D438,617 S | 3/2001 | Cooper et al. | |
| 6,206,903 B1 | 3/2001 | Ramans | |
| D441,076 S | 4/2001 | Cooper et al. | |
| 6,223,100 B1 | 4/2001 | Green | |
| D441,862 S | 5/2001 | Cooper et al. | |
| 6,238,415 B1 | 5/2001 | Sepetka et al. | |
| 6,240,312 B1 | 5/2001 | Alfano et al. | |
| 6,241,730 B1 | 6/2001 | Alby | |
| 6,244,809 B1 | 6/2001 | Wang et al. | |
| 6,246,200 B1 | 6/2001 | Blumenkranz et al. | |
| D444,555 S | 7/2001 | Cooper et al. | |
| 6,286,514 B1 | 9/2001 | Lemelson | |
| 6,292,678 B1 | 9/2001 | Hall et al. | |
| 6,293,282 B1 | 9/2001 | Lemelson | |
| 6,296,635 B1 | 10/2001 | Smith et al. | |
| 6,309,397 B1 | 10/2001 | Julian et al. | |
| 6,309,403 B1 | 10/2001 | Minor et al. | |
| 6,312,435 B1 | 11/2001 | Wallace et al. | |
| 6,321,106 B1 | 11/2001 | Lemelson | |
| 6,327,492 B1 | 12/2001 | Lemelson | |
| 6,331,181 B1 | 12/2001 | Tierney et al. | |
| 6,346,072 B1 | 2/2002 | Cooper | |
| 6,352,503 B1 | 3/2002 | Matsui et al. | |
| 6,364,888 B1 | 4/2002 | Niemeyer et al. | |
| 6,371,952 B1 | 4/2002 | Madhani et al. | |
| 6,394,998 B1 | 5/2002 | Wallace et al. | |
| 6,398,726 B1 | 6/2002 | Ramans et al. | |
| 6,400,980 B1 | 6/2002 | Lemelson | |
| 6,408,224 B1 | 6/2002 | Okamoto et al. | |
| 6,424,885 B1 | 7/2002 | Niemeyer et al. | |
| 6,432,112 B2 | 8/2002 | Brock et al. | |
| 6,436,107 B1 | 8/2002 | Wang et al. | |
| 6,441,577 B2 | 8/2002 | Blumenkranz et al. | |
| 6,450,104 B1 | 9/2002 | Grant et al. | |
| 6,451,027 B1 | 9/2002 | Cooper et al. | |
| 6,454,758 B1 | 9/2002 | Thompson et al. | |
| 6,459,926 B1 | 10/2002 | Nowlin et al. | |
| 6,463,361 B1 | 10/2002 | Wang et al. | |
| 6,468,203 B2 | 10/2002 | Belson | |
| 6,468,265 B1 | 10/2002 | Evans et al. | |
| 6,470,236 B2 | 10/2002 | Ohtsuki | |
| 6,491,691 B1 | 12/2002 | Morley et al. | |
| 6,491,701 B2 | 12/2002 | Tierney et al. | |
| 6,493,608 B1 | 12/2002 | Niemeyer et al. | |
| 6,496,099 B2 | 12/2002 | Wang et al. | |
| 6,508,413 B2 | 1/2003 | Bauer et al. | |
| 6,512,345 B2 | 1/2003 | Borenstein | |
| 6,522,906 B1 | 2/2003 | Salisbury, Jr. et al. | |
| 6,544,276 B1 | 4/2003 | Azizi | |
| 6,548,982 B1 | 4/2003 | Papanikolopoulos et al. | |
| 6,554,790 B1 | 4/2003 | Moll | |
| 6,565,554 B1 | 5/2003 | Niemeyer | |
| 6,574,355 B2 | 6/2003 | Green | |
| 6,587,750 B2 | 7/2003 | Gerbi et al. | |
| 6,591,239 B1 | 7/2003 | McCall et al. | |
| 6,594,552 B1 | 7/2003 | Nowlin et al. | |
| 6,610,007 B2 | 8/2003 | Belson et al. | |
| 6,620,173 B2 | 9/2003 | Gerbi et al. | |

(56) References Cited

U.S. PATENT DOCUMENTS

| | | |
|---|---|---|
| 6,642,836 B1 | 11/2003 | Wang et al. |
| 6,645,196 B1 | 11/2003 | Nixon et al. |
| 6,646,541 B1 | 11/2003 | Wang et al. |
| 6,648,814 B2 | 11/2003 | Kim et al. |
| 6,659,939 B2 | 12/2003 | Moll et al. |
| 6,661,571 B1 | 12/2003 | Shioda et al. |
| 6,671,581 B2 | 12/2003 | Niemeyer et al. |
| 6,676,684 B1 | 1/2004 | Morley et al. |
| 6,684,129 B2 | 1/2004 | Salisbury, Jr. et al. |
| 6,685,648 B2 | 2/2004 | Flaherty et al. |
| 6,685,698 B2 | 2/2004 | Morley et al. |
| 6,687,571 B1 | 2/2004 | Byme et al. |
| 6,692,485 B1 | 2/2004 | Brock et al. |
| 6,699,177 B1 | 3/2004 | Wang et al. |
| 6,699,235 B2 | 3/2004 | Wallace et al. |
| 6,702,734 B2 | 3/2004 | Kim et al. |
| 6,702,805 B1 | 3/2004 | Stuart |
| 6,714,839 B2 | 3/2004 | Salisbury, Jr. et al. |
| 6,714,841 B1 | 3/2004 | Wright et al. |
| 6,719,684 B2 | 4/2004 | Kim et al. |
| 6,720,988 B1 | 4/2004 | Gere et al. |
| 6,726,699 B1 | 4/2004 | Wright et al. |
| 6,728,599 B2 | 4/2004 | Wright et al. |
| 6,730,021 B2 | 5/2004 | Vassiliades, Jr. et al. |
| 6,731,988 B1 | 5/2004 | Green |
| 6,746,443 B1 | 6/2004 | Morley et al. |
| 6,764,441 B2 | 7/2004 | Chiel et al. |
| 6,764,445 B2 | 7/2004 | Ramans et al. |
| 6,766,204 B2 | 7/2004 | Niemeyer et al. |
| 6,770,081 B1 | 8/2004 | Cooper et al. |
| 6,774,597 B1 | 8/2004 | Borenstein |
| 6,776,165 B2 | 8/2004 | Jin |
| 6,780,184 B2 | 8/2004 | Tanrisever |
| 6,783,524 B2 | 8/2004 | Anderson et al. |
| 6,785,593 B2 | 8/2004 | Wang et al. |
| 6,788,018 B1 | 9/2004 | Blumenkranz |
| 6,793,653 B2 | 9/2004 | Sanchez et al. |
| 6,799,065 B1 | 9/2004 | Niemeyer |
| 6,799,088 B2 | 9/2004 | Wang et al. |
| 6,801,325 B2 | 10/2004 | Farr et al. |
| 6,804,581 B2 | 10/2004 | Wang et al. |
| 6,810,281 B2 | 10/2004 | Brock et al. |
| 6,817,972 B2 | 11/2004 | Snow |
| 6,817,974 B2 | 11/2004 | Cooper et al. |
| 6,817,975 B1 | 11/2004 | Farr et al. |
| 6,820,653 B1 | 11/2004 | Schempf et al. |
| 6,824,508 B2 | 11/2004 | Kim et al. |
| 6,824,510 B2 | 11/2004 | Kim et al. |
| 6,832,988 B2 | 12/2004 | Sprout |
| 6,832,996 B2 | 12/2004 | Woloszko et al. |
| 6,836,703 B2 | 12/2004 | Wang et al. |
| 6,837,846 B2 | 1/2005 | Jaffe et al. |
| 6,837,883 B2 | 1/2005 | Moll et al. |
| 6,839,612 B2 | 1/2005 | Sanchez et al. |
| 6,840,938 B1 | 1/2005 | Morley et al. |
| 6,852,107 B2 | 2/2005 | Wang et al. |
| 6,858,003 B2 | 2/2005 | Evans et al. |
| 6,860,346 B2 | 3/2005 | Burt et al. |
| 6,860,877 B1 | 3/2005 | Sanchez et al. |
| 6,866,671 B2 | 3/2005 | Tiemey et al. |
| 6,870,343 B2 | 3/2005 | Borenstein et al. |
| 6,871,117 B2 | 3/2005 | Wang et al. |
| 6,871,563 B2 | 3/2005 | Choset et al. |
| 6,879,880 B2 | 4/2005 | Nowlin et al. |
| 6,892,112 B2 | 5/2005 | Wang et al. |
| 6,899,705 B2 | 5/2005 | Niemeyer |
| 6,902,560 B1 | 6/2005 | Morley et al. |
| 6,905,460 B2 | 6/2005 | Wang et al. |
| 6,905,491 B1 | 6/2005 | Wang et al. |
| 6,911,916 B1 | 6/2005 | Wang et al. |
| 6,917,176 B2 | 7/2005 | Schempf et al. |
| 6,933,695 B2 | 8/2005 | Blumenkranz |
| 6,936,001 B1 | 8/2005 | Snow |
| 6,936,003 B2 | 8/2005 | Iddan |
| 6,936,042 B2 | 8/2005 | Wallace et al. |
| 6,943,663 B2 | 9/2005 | Wang et al. |
| 6,949,096 B2 | 9/2005 | Davison et al. |
| 6,951,535 B2 | 10/2005 | Ghodoussi et al. |
| 6,965,812 B2 | 11/2005 | Wang et al. |
| 6,974,411 B2 | 12/2005 | Belson |
| 6,974,449 B2 | 12/2005 | Niemeyer |
| 6,979,423 B2 | 12/2005 | Moll |
| 6,984,203 B2 | 1/2006 | Tartaglia et al. |
| 6,984,205 B2 | 1/2006 | Gazdzinski |
| 6,991,627 B2 | 1/2006 | Madhani et al. |
| 6,993,413 B2 | 1/2006 | Sunaoshi |
| 6,994,703 B2 | 2/2006 | Wang et al. |
| 6,994,708 B2 | 2/2006 | Manzo |
| 6,997,908 B2 | 2/2006 | Carrillo, Jr. et al. |
| 7,025,064 B2 | 4/2006 | Wang et al. |
| 7,027,892 B2 | 4/2006 | Wang et al. |
| 7,033,344 B2 | 4/2006 | Imran |
| 7,039,453 B2 | 5/2006 | Mullick |
| 7,042,184 B2 | 5/2006 | Oleynikov et al. |
| 7,048,745 B2 | 5/2006 | Tierney et al. |
| 7,053,752 B2 | 5/2006 | Wang et al. |
| 7,063,682 B1 | 6/2006 | Whayne et al. |
| 7,066,879 B2 | 6/2006 | Fowler et al. |
| 7,066,926 B2 | 6/2006 | Wallace et al. |
| 7,074,179 B2 | 7/2006 | Wang et al. |
| 7,077,446 B2 | 7/2006 | Kameda et al. |
| 7,083,571 B2 | 8/2006 | Wang et al. |
| 7,083,615 B2 | 8/2006 | Peterson et al. |
| 7,087,049 B2 | 8/2006 | Nowlin et al. |
| 7,090,683 B2 | 8/2006 | Brock et al. |
| 7,097,640 B2 | 8/2006 | Wang et al. |
| 7,105,000 B2 | 9/2006 | McBrayer |
| 7,107,090 B2 | 9/2006 | Salisbury, Jr. et al. |
| 7,109,678 B2 | 9/2006 | Kraus et al. |
| 7,118,582 B1 | 10/2006 | Wang et al. |
| 7,121,781 B2 | 10/2006 | Sanchez et al. |
| 7,125,403 B2 | 10/2006 | Julian et al. |
| 7,126,303 B2 | 10/2006 | Farritor et al. |
| 7,147,650 B2 | 12/2006 | Lee |
| 7,155,315 B2 | 12/2006 | Niemeyer et al. |
| 7,169,141 B2 | 1/2007 | Brock et al. |
| 7,182,025 B2 | 2/2007 | Ghorbel et al. |
| 7,182,089 B2 | 2/2007 | Ries |
| 7,199,545 B2 | 4/2007 | Oleynikov et al. |
| 7,206,626 B2 | 4/2007 | Quaid, III |
| 7,206,627 B2 | 4/2007 | Abovitz et al. |
| 7,210,364 B2 | 5/2007 | Ghorbel et |
| 7,214,230 B2 | 5/2007 | Brock et al. |
| 7,217,240 B2 | 5/2007 | Snow |
| 7,239,940 B2 | 7/2007 | Wang et al. |
| 7,250,028 B2 | 7/2007 | Julian et al. |
| 7,259,652 B2 | 8/2007 | Wang et al. |
| 7,273,488 B2 | 9/2007 | Nakamura et al. |
| 7,311,107 B2 | 12/2007 | Harel et al. |
| 7,339,341 B2 | 3/2008 | Oleynikov et al. |
| 7,372,229 B2 | 5/2008 | Farritor et al. |
| 7,447,537 B1 | 11/2008 | Funda et al. |
| 7,492,116 B2 | 2/2009 | Oleynikov et al. |
| 7,566,300 B2 | 7/2009 | Devierre et al. |
| 7,574,250 B2 | 8/2009 | Niemeyer |
| 7,637,905 B2 | 12/2009 | Saadat et al. |
| 7,645,230 B2 | 1/2010 | Mikkaichi et al. |
| 7,655,004 B2 | 2/2010 | Long |
| 7,670,329 B2 | 3/2010 | Flaherty et al. |
| 7,727,163 B2 * | 6/2010 | Behl .......................... 600/562 |
| 7,731,727 B2 | 6/2010 | Sauer |
| 7,762,825 B2 | 7/2010 | Burbank et al. |
| 7,772,796 B2 | 8/2010 | Farritor et al. |
| 7,785,251 B2 | 8/2010 | Wilk |
| 7,785,333 B2 | 8/2010 | Miyamoto et al. |
| 7,789,825 B2 | 9/2010 | Nobis et al. |
| 7,794,494 B2 | 9/2010 | Sahatjian et al. |
| 7,865,266 B2 | 1/2011 | Moll et al. |
| 7,960,935 B2 | 6/2011 | Farritor et al. |
| 8,179,073 B2 | 5/2012 | Farritor et al. |
| 2001/0018591 A1 | 8/2001 | Brock et al. |
| 2001/0049497 A1 | 12/2001 | Kalloo et al. |
| 2002/0003173 A1 | 1/2002 | Bauer et al. |
| 2002/0026186 A1 | 2/2002 | Woloszko et al. |

(56) References Cited

U.S. PATENT DOCUMENTS

| | | |
|---|---|---|
| 2002/0038077 A1* | 3/2002 | de la Torre et al. ........... 600/203 |
| 2002/0065507 A1 | 5/2002 | Azizi |
| 2002/0091374 A1 | 7/2002 | Cooper |
| 2002/0103417 A1 | 8/2002 | Gazdzinski |
| 2002/0111535 A1 | 8/2002 | Kim et al. |
| 2002/0120254 A1 | 8/2002 | Julian et al. |
| 2002/0128552 A1* | 9/2002 | Nowlin et al. ................ 600/427 |
| 2002/0140392 A1 | 10/2002 | Borenstein et al. |
| 2002/0147487 A1 | 10/2002 | Sundquist et al. |
| 2002/0151906 A1 | 10/2002 | Demarais et al. |
| 2002/0156347 A1 | 10/2002 | Kim et al. |
| 2002/0171385 A1 | 11/2002 | Kim et al. |
| 2002/0173700 A1 | 11/2002 | Kim et al. |
| 2002/0190682 A1 | 12/2002 | Schempf et al. |
| 2003/0020810 A1 | 1/2003 | Takizawa et al. |
| 2003/0045888 A1 | 3/2003 | Brock et al. |
| 2003/0065250 A1 | 4/2003 | Chiel et al. |
| 2003/0089267 A1 | 5/2003 | Ghorbel et al. |
| 2003/0092964 A1 | 5/2003 | Kim et al. |
| 2003/0097129 A1 | 5/2003 | Davison et al. |
| 2003/0100817 A1 | 5/2003 | Wang et al. |
| 2003/0114731 A1 | 6/2003 | Cadeddu et al. |
| 2003/0135203 A1 | 7/2003 | Wang et al. |
| 2003/0139742 A1 | 7/2003 | Wampler et al. |
| 2003/0144656 A1 | 7/2003 | Ocel et al. |
| 2003/0167000 A1 | 9/2003 | Mullick et al. |
| 2003/0172871 A1 | 9/2003 | Scherer |
| 2003/0179308 A1 | 9/2003 | Zamorano et al. |
| 2003/0181788 A1 | 9/2003 | Yokoi et al. |
| 2003/0229268 A1 | 12/2003 | Uchiyama et al. |
| 2003/0230372 A1 | 12/2003 | Schmidt |
| 2004/0024311 A1 | 2/2004 | Quaid |
| 2004/0034282 A1 | 2/2004 | Quaid |
| 2004/0034283 A1 | 2/2004 | Quaid |
| 2004/0034302 A1 | 2/2004 | Abovitz et al. |
| 2004/0050394 A1 | 3/2004 | Jin |
| 2004/0070822 A1 | 4/2004 | Shioda et al. |
| 2004/0099175 A1 | 5/2004 | Perrot et al. |
| 2004/0106916 A1 | 6/2004 | Quaid et al. |
| 2004/0111113 A1 | 6/2004 | Nakamura et al. |
| 2004/0138552 A1 | 7/2004 | Harel et al. |
| 2004/0140786 A1 | 7/2004 | Borenstein |
| 2004/0153057 A1 | 8/2004 | Davison |
| 2004/0173116 A1 | 9/2004 | Ghorbel et al. |
| 2004/0176664 A1 | 9/2004 | Iddan |
| 2004/0215331 A1 | 10/2004 | Chew et al. |
| 2004/0225229 A1 | 11/2004 | Viola |
| 2004/0254680 A1 | 12/2004 | Sunaoshi |
| 2004/0267326 A1 | 12/2004 | Ocel et al. |
| 2005/0014994 A1 | 1/2005 | Fowler et al. |
| 2005/0029978 A1 | 2/2005 | Oleynikov et al. |
| 2005/0043583 A1 | 2/2005 | Killmann et al. |
| 2005/0049462 A1 | 3/2005 | Kanazawa |
| 2005/0054901 A1 | 3/2005 | Yoshino |
| 2005/0054902 A1 | 3/2005 | Konno |
| 2005/0064378 A1 | 3/2005 | Toly |
| 2005/0065400 A1 | 3/2005 | Banik et al. |
| 2005/0083460 A1 | 4/2005 | Hattori et al. |
| 2005/0096502 A1 | 5/2005 | Khalili |
| 2005/0143644 A1 | 6/2005 | Gilad et al. |
| 2005/0154376 A1 | 7/2005 | Riviere et al. |
| 2005/0165449 A1 | 7/2005 | Cadeddu et al. |
| 2005/0203344 A1* | 9/2005 | Orban et al. ................ 600/204 |
| 2005/0283137 A1 | 12/2005 | Doyle et al. |
| 2005/0288555 A1 | 12/2005 | Binmoeller |
| 2005/0288665 A1 | 12/2005 | Woloszko |
| 2006/0020272 A1 | 1/2006 | Gildenberg |
| 2006/0046226 A1 | 3/2006 | Bergler et al. |
| 2006/0119304 A1 | 6/2006 | Farritor et al. |
| 2006/0149135 A1 | 7/2006 | Paz |
| 2006/0152591 A1 | 7/2006 | Lin |
| 2006/0155263 A1 | 7/2006 | Lipow |
| 2006/0195015 A1 | 8/2006 | Mullick et al. |
| 2006/0196301 A1 | 9/2006 | Oleynikov et al. |
| 2006/0198619 A1 | 9/2006 | Oleynikov et al. |
| 2006/0241570 A1 | 10/2006 | Wilk |
| 2006/0241732 A1 | 10/2006 | Denker et al. |
| 2006/0253109 A1 | 11/2006 | Chu |
| 2006/0258954 A1 | 11/2006 | Timberlake et al. |
| 2007/0032701 A1 | 2/2007 | Fowler et al. |
| 2007/0043397 A1 | 2/2007 | Ocel et al. |
| 2007/0055342 A1 | 3/2007 | Wu et al. |
| 2007/0080658 A1 | 4/2007 | Farritor et al. |
| 2007/0106113 A1 | 5/2007 | Ravo |
| 2007/0123748 A1 | 5/2007 | Meglan |
| 2007/0142725 A1* | 6/2007 | Hardin et al. ................ 600/431 |
| 2007/0156019 A1 | 7/2007 | Larkin et al. |
| 2007/0156211 A1 | 7/2007 | Ferren et al. |
| 2007/0161864 A1* | 7/2007 | Sloan ............................ 600/204 |
| 2007/0167955 A1 | 7/2007 | De La Menardiere et al. |
| 2007/0225633 A1 | 9/2007 | Ferren et al. |
| 2007/0225634 A1 | 9/2007 | Ferren et al. |
| 2007/0241714 A1 | 10/2007 | Okeynikov et al. |
| 2007/0244520 A1 | 10/2007 | Ferren et al. |
| 2007/0250064 A1* | 10/2007 | Darois et al. .................... 606/73 |
| 2007/0255273 A1 | 11/2007 | Fernandez et al. |
| 2008/0004634 A1 | 1/2008 | Farritor et al. |
| 2008/0015565 A1 | 1/2008 | Davison |
| 2008/0015566 A1 | 1/2008 | Livneh |
| 2008/0033569 A1 | 2/2008 | Ferren et al. |
| 2008/0058835 A1 | 3/2008 | Farritor et al. |
| 2008/0058989 A1 | 3/2008 | Oleynikov et al. |
| 2008/0103440 A1 | 5/2008 | Ferren et al. |
| 2008/0111513 A1 | 5/2008 | Farritor et al. |
| 2008/0119870 A1 | 5/2008 | Williams et al. |
| 2008/0132890 A1 | 6/2008 | Woloszko et al. |
| 2008/0164079 A1 | 7/2008 | Jacobsen |
| 2008/0183033 A1 | 7/2008 | Bern et al. |
| 2008/0221591 A1 | 9/2008 | Farritor et al. |
| 2008/0269557 A1 | 10/2008 | Marescaux et al. |
| 2009/0020724 A1 | 1/2009 | Paffrath |
| 2009/0024142 A1* | 1/2009 | Ruiz Morales ................ 606/130 |
| 2009/0048612 A1 | 2/2009 | Farritor et al. |
| 2009/0054909 A1 | 2/2009 | Farritor et al. |
| 2009/0069821 A1 | 3/2009 | Farritor et al. |
| 2009/0076536 A1 | 3/2009 | Rentschler et al. |
| 2009/0137952 A1* | 5/2009 | Ramamurthy et al. .... 604/95.01 |
| 2009/0143787 A9 | 6/2009 | De La Pena |
| 2009/0163929 A1 | 6/2009 | Yeung et al. |
| 2009/0171373 A1 | 7/2009 | Farritor et al. |
| 2009/0234369 A1 | 9/2009 | Bax et al. |
| 2009/0236400 A1* | 9/2009 | Cole et al. ................... 227/180.1 |
| 2009/0240246 A1 | 9/2009 | Devill et al. |
| 2009/0247821 A1 | 10/2009 | Rogers |
| 2009/0248038 A1 | 10/2009 | Blumenkranz et al. |
| 2009/0281377 A1* | 11/2009 | Newell et al. ................ 600/104 |
| 2009/0305210 A1 | 12/2009 | Guru et al. |
| 2010/0010294 A1* | 1/2010 | Conlon et al. ................ 600/104 |
| 2010/0016659 A1 | 1/2010 | Weitzner |
| 2010/0042097 A1 | 2/2010 | Newton et al. |
| 2010/0056863 A1 | 3/2010 | Dejima et al. |
| 2010/0069710 A1 | 3/2010 | Yamatani et al. |
| 2010/0069940 A1 | 3/2010 | Miller et al. |
| 2010/0081875 A1 | 4/2010 | Fowler et al. |
| 2010/0139436 A1 | 6/2010 | Kawashima et al. |
| 2010/0198231 A1 | 8/2010 | Scott |
| 2010/0204713 A1 | 8/2010 | Ruiz |
| 2010/0245549 A1 | 9/2010 | Allen et al. |
| 2010/0262162 A1 | 10/2010 | Omori |
| 2010/0318059 A1 | 12/2010 | Farritor et al. |
| 2011/0015569 A1 | 1/2011 | Kirschenman et al. |
| 2011/0020779 A1 | 1/2011 | Hannaford et al. |
| 2011/0071347 A1 | 3/2011 | Rogers et al. |
| 2011/0077478 A1 | 3/2011 | Freeman et al. |
| 2011/0152615 A1 | 6/2011 | Schostek et al. |
| 2011/0224605 A1 | 9/2011 | Farritor et al. |
| 2011/0230894 A1 | 9/2011 | Simaan et al. |
| 2011/0237890 A1 | 9/2011 | Farritor et al. |
| 2011/0238080 A1 | 9/2011 | Ranjit et al. |
| 2011/0270443 A1 | 11/2011 | Kamiya et al. |
| 2012/0035582 A1 | 2/2012 | Nelson et al. |
| 2012/0095492 A1* | 4/2012 | Babkes et al. ................ 606/192 |
| 2012/0109150 A1 | 5/2012 | Quaid et al. |

(56) References Cited

U.S. PATENT DOCUMENTS

| | | |
|---|---|---|
| 2012/0253515 A1 | 10/2012 | Coste-Maniere et al. |
| 2013/0041360 A1 | 2/2013 | Farritor |
| 2013/0131695 A1 | 5/2013 | Scarfogliero et al. |

FOREIGN PATENT DOCUMENTS

| | | |
|---|---|---|
| JP | 5115425 | 5/1993 |
| JP | 200716235 | 6/1993 |
| JP | 2006507809 | 9/1994 |
| JP | 07 136173 | 5/1995 |
| JP | 7306155 | 11/1995 |
| JP | 08-224248 | 9/1996 |
| JP | 2003220065 | 8/2003 |
| JP | 2004322310 | 6/2004 |
| JP | 2004180781 | 7/2004 |
| JP | 2004329292 | 11/2004 |
| JP | 2006508049 | 3/2006 |
| WO | WO 92/21291 | 12/1992 |
| WO | WO 02/082979 | 10/2002 |
| WO | WO 02/100256 | 12/2002 |
| WO | WO 2005/009211 | 2/2005 |
| WO | WO 2006 005075 | 1/2006 |
| WO | WO 2006/079108 | 1/2006 |
| WO | WO 2006/052927 | 5/2006 |
| WO | WO 2007/111571 | 10/2007 |
| WO | WO 2007/149559 | 12/2007 |
| WO | WO 2009023851 A1 | 8/2008 |
| WO | WO 2009/144729 | 12/2009 |
| WO | WO2010/042611 | 4/2010 |
| WO | WO2010/046823 | 4/2010 |
| WO | WO 2011/118646 A1 | 9/2011 |
| WO | WO 2011/135503 A1 | 11/2011 |
| WO | WO 2013009887 | 1/2013 |

OTHER PUBLICATIONS

Patronik et al., "Preliminary evaluation of a mobile robotic device for navigation and intervention on the beating heart," Computer Aided Surgery, 10(4): 225-232, Jul. 2005.

Peirs et al., "A miniature manipulator for integration in a self-propelling endoscope," Sensors and Actuators A, 2001, 92: 343-349.

Peters, "Minimally Invasive Colectomy: Are the Potential Benefits Realized?" Dis Colon Rectum 1993; 36: 751-756.

Phee et al., "Analysis and Development of Locomotion Devices for the Gastrointestinal Tract," IEEE Transaction on Biomedical Engineering, vol. 49, No. 6, Jun. 2002, pp. 613-616.

Phee et al., "Development of Microrobotic Devices for Locomotion in the Human Gastrointestinal Tract," International Conference on Computational Intelligence, Robotics and Autonomous Systems (CIRAS 2001), Nov. 28-30, (2001), Singapore.

Platt et al., "In Vivo Robotic Cameras can Enhance Imaging Capability During Laparoscopic Surgery," in the Proceedings of the Society of American Gastrointestinal Endoscopic Surgeons (SAGES) Scientific Conference, Ft. Lauderdale, FL, Apr. 13-16, 2005, I pg.

Preliminary Amendment filed Apr. 11, 2007, in related case U.S. Appl. No. 11/403,756, 7 pp.

Preliminary Amendment filed Jul. 30, 2008, in related case U.S. Appl. No. 12/171,413, 4 pp.

RCE and Amendment filed Jun. 13, 2007, in related case U.S. Appl. No. 11/403,756, 8 pp.

Rentschler et al., "Mobile In Vivo Biopsy and Camera Robot," Studies in Health and Infonnatics Medicine Meets Virtual Reality, vol. 119., pp. 449-454, IOS Press, Long Beach, CA, 2006e.

Rentschler et al., "Mobile In Vivo Biopsy Robot," IEEE International Conference on Robotics and Automation, Orlando, Florida, May 2006, pp. 4155-4160.

Rentschler et al., "Miniature in vivo Robots for Remote and Harsh Environments," IEEE Transactions on Information Technology in Biomedicine, Jan. 2006; 12(1): 66-75.

Rentschler et al., "An In Vivo Mobile Robot for Surgical Vision and Task Assistance," Journal of Medical Devices, Mar. 2007, vol. 1: 23-29.

Rentschler et al., "In vivo Robotics during the NEEMO 9 Mission," Medicine Meets Virtual Reality, Feb. 2007, I pg.

Rentschler et al., "In Vivo Robots for Laparoscopic Surgery," Studies in Health Technology and Infonnatics—Medicine Meets Virtual Reality, ISO Press, Newport Beach, CA, 2004a, 98: 316-322.

Rentschler et al., "Mechanical Design of Robotic In Vivo Wheeled Mobility," ASME Journal of Mechanical Design, 2006a, pp, I-II.

Rentschler et al., "Mobile In Vivo Camera Robots Provide Sole Visual Feedback for Abdominal Exploration and Cholecystectomy," Journal of Surgical Endoscopy, 20-I: 135-138, 2006b.

Rentschler et al., "Mobile In Vivo Robots Can Assist in Abdominal Exploration," from the Proceedings of the Society of American Gastrointestinal Endoscopic Surgeons (SAGES) Scientific Conference, Ft. Lauderdale, FL, Apr. 13-16, 2005b.

Rentschler et al., "Modeling, Analysis, and Experimental Study of In Vivo Wheeled Robotic Mobility," IEEE Transactions on Robotics, 22 (2): 308-321, 2005c.

Rentschler et al., "Natural Orifice Surgery with an Endoluminal Mobile Robot," The Society of American Gastrointestinal Endoscopic Surgeons, Dallas, TX, Apr. 2006d, 14 pp.

Rentschler et al., "Theoretical and Experimental Analysis of In Vivo Wheeled Mobility," ASME Design Engineering Technical Conferences: 28th Biennial Mechanisms and Robotics Conference, Salt Lake City, Utah, Sep. 28-Oct. 2, 2004, pp. 1-9.

Rentschler et al., "Toward In Vivo Mobility," Studies in Health Technology and Informatics—Medicine Meets Virtual Reality, ISO Press, Long Beach, CA, 2005a, III: 397-403.

Response to Rule 312 Amendment in related case U.S. Appl. No. 11/695,944, dated Jan. 12, 2009, 2 pp.

Riviere et al., "Toward Active Tremor Canceling in Handheld Microsurgical Instruments," IEEE Transactions on Robotics and Automation, Oct. 2003, 19(5): 793-800.

Rosen et al., "Force Controlled and Teleoperated Endoscopic, Grasper for Minimally Invasive Surgery—Experimental Performance Evaluation," IEEE Transactions of Biomedical Engineering, Oct. 1999; 46(10): 1212-1221.

Rosen et al., "Objective Laparoscopic Skills Assessments of Surgical Residents Using Hidden Markov Models Based on Haptic Information and Tool/Tissue Interactions," Studies in Health Technology and Informatics—Medicine Meets Virtual Reality, Jan. 2001, 7 pp.

Rosen et al., "Spherical Mechanism Analysis of a Surgical Robot for Minimally Invasive Surgery—Analytical and Experimental Approaches," Studies in Health Technology and Informatics—Medicine Meets Virtual Reality, pp. 442-448, Jan. 2005.

Rosen et al., "Task Decomposition of Laparoscopic Surgery for Objective Evaluation of Surgical Residents' Learning Curve Using Hidden Markov Model," Computer Aided Surgery, vol. 7, pp. 49-61, 2002.

Rosen et al., "The Blue DRAGON—A System of Measuring the Kinematics and the Dynamics of Minimally Invasive Surgical Tools In-Vivo," Proc. of the 2002 IEEE International Conference on Robotics and Automation, Washington, DC, pp. 1876-1881, May 2002.

Ruurda et al., "Robot-Assisted surgical systems: a new era in laparoscopic surgery," Ann R. Coll Surg Engl., 2002; 84: 223-226.

Ruurda et al., "Feasibility of Robot-Assisted Laparoscopic Surgery," Surgical Laparoscopy, Endoscopy & Percutaneous Techniques, 2002; 12(1):41-45.

Sackier et al., "Robotically assisted laparoscopic surgery," Surgical Endoscopy, 1994; 8: 63-66.

Salky, "What is the Penetration of Endoscopic Techniques into Surgical Practice?" Digestive Surgery, 2000; 17:422-426.

Satava, "Surgical Robotics: The Early Chronicles," Surgical Laparoscopy, Endoscopy & Percutaneous Techniques, 2002; 12(1): 6-16.

Schippers et al., (1996) "Requirements and Possibilities of Computer-Assisted Endoscopic Surgery," In: Computer Integrated Surgery: Technology and Clinical Applications, pp. 561-565.

Schurr et al., "Robotics and Telemanipulation Technologies for Endoscopic Surgery," Surgical Endoscopy, 2000; 14: 375-381.

Schwartz, "In the Lab: Robots that Slink and Squirm," The New York Times, Mar. 27, 2007, 4 pp.

Sharp LL-151-3D, http://www.sharp3d.com, 2006, 2 pp.

(56) References Cited

OTHER PUBLICATIONS

Slatkin et al., "The Development of a Robotic Endoscope," Proceedings of the 1995 IEEE International Conference on Robotics and Automation, pp. 162-171, 1995.
Smart Pill "Fastastic Voyage: Smart Pill to Expand Testing," http://www.smartpilldiagnostics.com, Apr. 13, 2005, 1 pg.
Southern Surgeons Club (1991), "A prospective analysis of 1518 laparoscopic cholecystectomies," N. Eng. 1 Med. 324 (16): 1073-1078.
Stefanini et al., "Modeling and Experiments on a Legged Microrobot Locomoting in a Tubular Compliant and Slippery Environment," Int. Journal of Robotics Research, vol. 25, No. 5-6, pp. 551-560, May-Jun. 2006.
Stiff et al.., "Long-term Pain: Less Common After Laparoscopic than Open Cholecystectomy," British Journal of Surgery, 1994; 81: 1368-1370.
Strong, et al., "Efficacy of Novel Robotic Camera vs. a Standard Laproscopic Camera," Surgical Innovation vol. 12, No. 4, Dec. 2005, Westminster Publications, Inc., pp. 315-318.
Suzumori et al., "Development of Flexible Microactuator and its Applications to Robotics Mechanisms," Proceedings of the IEEE International Conference on Robotics and Automation, 1991: 1622-1627.
Taylor et al., "A Telerobotic Assistant for Laparoscopic Surgery," IEEE Eng Med Biol, 1995; 279-287.
Tendick et al.. (1993), "Sensing and Manipulation Problems in Endoscopic Surgery: Experiment, Analysis, and Observation," Presence 2( 1): 66-81.
Abbott et al., "Design of an Endoluminal NOTES Robotic System," from the Proceedings of the 2007 IEEE/RSJ Int'l Conf. on Intelligent Robot Systems, San Diego, CA, Oct. 29-Nov. 2, 2007, pp. 410-416.
Allendorf et al., "Postoperative Immune Function Varies Inversely with the Degree of Surgical Trauma in a Murine Model," Surgical Endoscopy 1997; 11:427-430.
Ang, "Active Tremor Compensation in Handheld Instrument for Microsurgery," Doctoral Dissertation, tech report CMU-RI-TR-04-28, Robotics Institute, Carnegie Mellon Unviersity, May 2004, 167pp.
Applicant Amendment after Notice of Allowance under Rule 312, filed Aug. 25, 2008, in related case U.S. Appl. No. 11/695,944, 6pp.
Applicant Response to Office Action dated Apr. 17, 2007, in related case U.S. Appl. No. 11/552,379, filed Aug. 8, 2007, 7 pp.
Applicant Response to Office Action dated Aug. 18, 2006, in related case U.S. Appl. No. 11/398,174, filed Nov. 7, 2006, 8pp.
Applicant Response to Office Action dated Aug. 21, 2006, in related case U.S. Appl. No. 11/403,756, filed Nov. 21, 2006, 52pp.
Applicant Response to Office Action dated Oct. 29, 2007, in related case U.S. Appl. No. 11/695,944, filed Jan. 22, 2008, 6pp.
Atmel 80C5X2 Core, http://www.atmel.com, 2006, 186pp.
Bailey et al., "Complications of Laparoscopic Surgery," Quality Medical Publishers, Inc., 1995, 25pp.
Ballantyne, "Robotic Surgery, Telerobotic Surgery, Telepresence, and Telementoring," Surgical Endoscopy, 2002; 16: 1389-1402.
Bauer et al., "Case Report: Remote Percutaneous Renal Percutaneous Renal Access Using a New Automated Telesurgical Robotic System," Telemedicine Journal and e-Health 2001; (4): 341-347.
Begos et al., "Laparoscopic Cholecystectomy: From Gimmick to Gold Standard," J Clin Gastroenterol, 1994; 19(4): 325-330.
Berg et al., "Surgery with Cooperative Robots," Medicine Meets Virtual Reality, Feb. 2007, 1 pg.
Breda et al., "Future developments and perspectives in laparoscopy," Eur. Urology 2001; 40(1): 84-91.
Breedveld et al., "Design of Steerable Endoscopes to Improve the Visual Perception of Depth During Laparoscopic Surgery," ASME, Jan. 2004; vol. 126, pp. 1-5.
Breedveld et al., "Locomotion through the Intestine by means of Rolling Stents," Proceedings of the ASME Design Engineering Technical Conferences, 2004, pp. 1-7.
Calafiore et al., Multiple Arterial Conduits Without Cardiopulmonary Bypass: Early Angiographic Results,: Ann Thorac Surg, 1999; 67: 450-456.
Camarillo et al., "Robotic Technology in Surgery: Past, Present and Future," The American Journal of Surgery, 2004; 188: 2S-15.
Cavusoglu et al, "Telesurgery and Surgical Simulation: Haptic Interfaces to Real and Virtual Surgical Environments," in McLaughliin, M.L., Hespanha, J.P., and Sukhatme, G., editors. Touch in virtual environments, IMSC Series in Multimedia 2001, 28pp.
Cavusoglu et al., "Robotics for Telesurgery: Second Generation Berkeley/UCSF Laparoscopic Telesurgical Workstation and Looking Towards the Future Applications," Industrial Robot: An International Journal, 2003; 30(1): 22-29.
Chanthasopeephan et al., (2003), "Measuring Forces in Liver Cutting: New Equipment and Experimenal Results," Annals of Biomedical Engineering 31: 1372-1382.
Choi et al., "Flexure-based Manipulator for Active Handheld Microsurgical Instrument," Proceedings of the 27th Annual International Conference of the IEEE Engineering in Medicine and Biology Society (EMBS), Sep. 2005, 4pp.
Cuschieri, "Technology for Minimal Access Surgery," BMJ, 1999, 319: 1-6.
Dakin et al., "Comparison of laparoscopic skills performance between standard instruments and two surgical robotic systems," Surg Endosc., 2003; 17: 574-579.
Dumpert et al., "Improving in Vivo Robot Visioin Quality," from the Proceedings of Medicine Meets Virtual Realtiy, Long Beach, CA, Jan. 26-29, 2005. 1 pg.
Dumpert et al., "Stereoscopic In Vivo Surgical Robots," IEEE Sensors Special Issue on In Vivo Sensors for Medicine, Jan. 2007, 10 pp.
Examiner Interview Summary dated Aug. 6 and Aug. 12, 2008, in related case U.S. Appl. No. 11/695,944, 1 pg.
Examiner Interview Summary dated May 9, 2008, in related case U.S. Appl. No. 11/695,944, 1 pg.
Examiner Interview Summary dated Nov. 30, 2006, in related case U.S. Appl. No. 11/398,174, 2pp.
Falcone et al., "Robotic Surgery," Clin. Obstet. Gynecol. 2003, 46(1): 37-43.
Faraz et al., "Engineering Approaches to Mechanical and Robotic Design for Minimaly Invasive Surgery (MIS)," Kluwer Academic Publishers (Boston), 2000, 13pp.
Fearing et al., "Wing Transmission for a Micromechanical Flying Insect," Proceedings of the 2000 IEEE International Conference to Robotics & Automation, Apr. 2000; 1509-1516.
Fireman et al., "Diagnosing small bowel Crohn's desease with wireless capsule endoscopy," Gut 2003; 52: 390-392.
Franklin et al., "Prospective Comparison of Open vs. Laparoscopic Colon Surgery for Carcinoma: Five-Year Results," Dis Colon Rectum, 1996; 39: S35-S46.
Franzino, "The Laprotek Surgical System and the Next Generation of Robotics," Surg Clin North Am, 2003 83(6).
Fraulob et al., "Miniature assistance module for robot-assisted heart surgery," Biomed. Tech. 2002, 47 Suppl. 1, Pt. 1:12-15.
Fukuda et al., "Mechanism and Swimming Experiment of Micro Mobile Robot in Water," Proceedings of the 1994 IEEE International Conference on Robotics and Automation, 1994: 814-819.
Fukuda et al, "Micro Active Catheter System with Multi Degrees of Freedom," Proceedings of the IEEE International Conference on Robotics and Automation, May 1994, pp. 2290-2295.
Fuller et al., "Laparoscopic Trocar Injuries: A Report from a U.S. Food and Drug Administration (FDA) Center for Devices and Radiological Health (CDRH) Systematic Technology Assessment of Medical Products (STAMP) Committe," U.S. Food and Drug Adminstration, available at http://www.fdaJ:?;ov, Finalized: Nov. 7, 2003; Updated: Jun. 24, 2005, 11 pp.
Grady, "Doctors Try New Surgery for Gallbladder Removal," The New York Times, Apr. 20, 2007, 3 pp.
Guber et al., "Miniaturized Instrumetn Systems for Minimally Invasive Diagnosis and Therapy," Biomedizinishe Technic. 2002, Band 47, Erganmngsband 1, Teil 1.
International Preliminary Report on Patentability from related case PCT/US20071014567, mailed Jan. 8, 2009, 11 pp.

(56) References Cited

OTHER PUBLICATIONS

International Search report and Written Opinion from international application No. PCT/US2012/41911, mailed Mar. 13, 2013.
International Search Report and Written Opinion from international application No. PCT/US12/46274, mailed Sep. 25, 2012.
International Search Report and Written Opinion from international application No. PCT/US2007/089191, mailed Nov. 10, 2008, 20 pp.
"International Search Report and Written Opinion from international application No. PCT/US07/14567, mailed Apr. 28, 2008, 19 pp."
International Search Report and Written Opinion of international application No. PCT/US2008/069822, mailed Aug. 5, 2009, 12 pp.
International Search Report and Written Opinion of international application No. PCT/US2008/073334, mailed Jan. 12, 2009, 11 pp.
International Search Report and Written Opinion of international application No. PCT/US2008/073369, mailed Nov. 12, 2008, 12 pp.
International Search Report and Written Opinion issued in PCT/US11/46809, mailed Dec. 8, 2011.
Ishiyama et al., "Spiral-type Micro-machine for Medical Applications," 2000 International Symposium on Micromechatronics and Human Science, 2000: 65-69.
Jagannath et al., "Peroral transgastric endoscopic ligation of fallopian tubes with long-term survival in a porcine model," Gastrointestinal Endoscopy, 2005; 61(3): 449-453.
Kalloo et al., "Flexible transgastric peritoneoscopy: a novel approach to diagnostic and therapeutic interventions in the peritoneal cavity," Gastrointestinal Endoscopy, 2004; 60(1): 114-117.
Kang et al., "Robotic Assistants Aid Surgeons During Minimally Invasive Procedures," IEEE Engineering in Medicine and Biology, Jan.-Feb. 2001; pp. 94-104.
Kantsevoy et al., "Endoscopic gastrojejunostomy with survival in a porcine model," Gastrointestinal Endoscopy, 2005; 62(2): 287-292.
Kantsevoy et al., "Transgastric endoscopic splenectomy," Surgical Endoscopy, 2006; 20: 522-525.
Kazemier et al. (1998), "Vascular Injuries During Laparoscopy," J. Am. Coli. Surg. 186(5): 604-5.
Kim, "Early Experience with Telemanipulative Robot-Assisted Laparoscopic Cholecystectomy Using da Vinci," Surgical Laparoscopy, Endoscopy & Percutaneous Techniques, 2002; 12(1):33-40.
Ko et al., "Per-Oral transgastric abdominal surgery," Chinese Journal of Digestive Diseases, 2006; 7: 67-70.
Lafullarde et al., "Laparoscopic Nissen Fundoplication: Five-year Results and Beyond," Arch/Surg, Feb. 2001; 136:180-184.
Leggett et al. (2002), "Aortic injury during laparoscopic fundoplication," Surg. Endoscopy 16(2): 362.
Li et al. (2000), "Microvascular Anastomoses Performed in Rats Using a Microsurgical Telemanipulator," Comp. Aid. Surg. 5: 326-332.
Liem et al., "Comparison of Conventional Anterior Surgery and Laparoscopic Surgery for Inguinal-hernia Repair," New England Journal of Medicine, 1997; 336 (22): 1541-1547.
MacFarlane et al., "Force-Feedback Grasper Helps Restore the Sense of Touch in Minimally Invasive Surgery," Journal of Gastrointestinal Surgery, 1999; 3: 278-285.
Mack et al., "Present Role of Thoracoscopy in the Diagnosis and Treatment of Diseases of the Chest," Ann Thorac Surgery, 1992; 54: 403-409.
Mack, "Minimally Invasive and Robotic Surgery," JAMA, Feb. 2001; 285(5): 568-572.
Mei et al., "Wireless Drive and Control of a Swimming Microrobot," Proceedings of the 2002 IEEE International Conference on Robotics & Automation, May 2002: 1131-1136.
Melvin et al., "Computer-Enhanced vs. Standard Laparoscopic Antireflux Surgery," J Gastrointest Surg 2002; 6: 11-16.
Menciassi et al., "Locomotion of a Leffed Capsule in the Gastrointestinal Tract: Theoretical Study and Preliminary Technological Results," IEEE Int. Conf. on Engineering in Medicine and Biology, San Francisco, CA, pp. 2767-2770, Sep. 2004.
Menciassi et al., "Robotic Solutions and Mechanisms for a Semi-Autonomous Endoscope," Proceedings of the 2002 IEEE/RSJ Intl. Conference on Intelligent Robots and Systems, Oct. 2002; 1379-1384.
Menciassi et al., "Shape memory alloy clamping devices of a capsule for monitoring tasks in the gastrointestinal tract," J. Micromech. Microeng, 2005, 15: 2045-2055.
Meron, "The development of the swallowable video capsule (M2A)," Gastrointestinal Endoscopy 2000; 52 6: 817-819.
Micron, http://www.micron.com, 2006, I/4-inch VGA NTSC/PAL CMOS Digital Image Sensor, 98 pp.
Midday Jeff et al., "Material Handling System for Robotic natural Orifice Surgery", Proceedings of the 2011 Design of medical Devices Conference, Apr. 12-14, 2011, Minneapolis, MN, 4 pages.
Munro (2002), "Laparoscopic access: complications, technologies, and techniques," Curro Opin. Obstet. Gynecol., 14(4): 365-74.
Nio et al., "Efficiency of manual vs robotical (Zeus) assisted laparoscopic surgery in the performance of standardized tasks," Surg Endosc, 2002; 16: 412-415.
Office Action dated Apr. 17, 2007, received in related case U.S. Appl. No. 11/552,379, 5 pp.
Office Action dated Apr. 3, 2009, received in related case U.S. Appl. No. 11/932,516, 43 pp.
Office Action dated Aug. 18, 2006, received in related case U.S. Appl. No. 11/398,174, 6 pp.
Office Action dated Aug. 21, 2006, received in related case U.S. Appl. No. 11/403,756, 6 pp.
Office Action dated Oct. 29, 2007, received in related case U.S. Appl. No. 11/695,944, 6 pp.
Office Action dated Oct. 9, 2008, received in related case U.S. Appl. No. 11/932,441, 4 pp.
Oleynikov et al., "In Vivo Camera Robots Provide Improved Vision for Laparoscopic Surgery," Computer Assisted Radiology and Surgery (CARS), Chicago, IL, Jun. 23-26, 2004b.
Oleynikov et al., "In Vivo Robotic Laparoscopy," Surgical Innovation, Jun. 2005, 12(2): 177-181.
Oleynikov et al., "Miniature Robots Can Assist in Laparoscopic Cholecystectomy," Journal of Surgical Endoscopy, 19-4: 473-476, 2005.
O'Neill, "Surgeon takes new route to gallbladder," The Oregonian, Jun. 2007, 2 pp.
Orlando et al., (2003), "Needle and Trocar Injuries in Diagnostic Laparoscopy under Local Anesthesia: What Is the True Incidence of These Complications?" Journal of Laparoendoscopic & Advanced Surgical Techniques 13(3): 181-184.
Park et al., "Trocar-less Instrumentation for Laparoscopy: Magnetic Positioning of Intra-abdominal Camera and Retractor," Ann Surg, Mar. 2007; 245(3): 379-384.
Park et al., "Experimental studies of transgastric gallbladder surgery: cholecystectomy and cholecystogastric anastomosis (videos)," Gastrointestinal Endoscopy, 2005; 61(4): 601-606.
Tendick et al., "Applications of Micromechatronics in Minimally Invasive Surgery," IEEE/ASME Transactions on Mechatronics, 1998; 3(1): 34-42.
Thomann et al., "The Design of a new type of Micro Robot for the Intestinal Inspection," Proceedings of the 2002 IEEE Intl. Conference on Intelligent Robots and Systems, Oct. 2002: 1385-1390.
U.S. Appl. No. 60/180,960, filed Feb. 2000.
U.S. Appl. No. 60/956,032, filed Aug. 15, 2007.
U.S. Appl. No. 60/983,445, filed Oct. 29, 2007.
U.S. Appl. No. 60/990,062, filed Nov. 26, 2007.
U.S. Appl. No. 60/990,076, filed Nov. 26, 2007.
U.S. Appl. No. 60/990,086, filed Nov. 26, 2007.
U.S. Appl. No. 60/990,106, filed Nov. 26, 2007.
U.S. Appl. No. 60/990,470, filed Nov. 27, 2007.
U.S. Appl. No. 61/025,346, filed Feb. 1, 2008.
U.S. Appl. No. 61/030,588, filed Feb. 22, 2008.
U.S. Appl. No. 61/030,617, filed Feb. 22, 2008.
Way et al., (editors), "Fundamentals of Laparoscopic Surgery," Churchill Livingstone Inc., 1995, 14 pp.

(56) References Cited

OTHER PUBLICATIONS

Wolfe et al., "Endoscopic Cholecystectomy: an analysis of Complications," Arch. Surg. Oct. 1991; 126: 1192-1196.

Worn et al., "Espirit Project No. 33915: Miniaturised Robot for Micro Manipulation (MINIMAN)", Nov. 1998; http://www.ipr.ira.ujka.de/-microbot/miniman.

Yu et al., "Microrobotic Cell Injection," Proceedings of the 2001 IEEE International Conference on Robotics and Automation, May 2001; 620-625.

International Search Report and Written Opinion of international application No. PCT/US2010/061137, mailed Feb. 11, 2011, 10 pp.

Abbou et al., "Laparoscopic Radical Prostatectomy with a Remote Controlled Robot," The Journal of Urology, Jun. 2001, 165: 1964-1966.

Glukhovsky et al.., "The development and application of wireless capsule endoscopy," Int. J. Med. Robot. Comput. Assist. Surgery, 2004; I(1): 114-123.

Gong et al., Wireless endoscopy, Gastrointestinal Endoscopy 2000; 51(6): 725-729.

Hanly et al., "Value of the SAGES Learning Center in introducing new technology," Surgical Endoscopy, 2004; 19 (4): 477-483.

Palm, William, "Rapid Prototyping Primer" May 1998 (revised Jul. 30, 2002) (htlp://www.me.psu.edu/lamancusa/rapidpro/primer/chapter2.htm).

* cited by examiner

METHODS AND SYSTEMS FOR HANDLING OR DELIVERING MATERIALS FOR NATURAL ORIFICE SURGERY

CROSS-REFERENCE TO RELATED APPLICATION

This application claims priority to Provisional Application No. 61/371,361, filed Aug. 6, 2010, which is herein incorporated by reference in its entirety.

STATEMENT REGARDING FEDERALLY SPONSORED RESEARCH OR DEVELOPMENT

This invention was made with government support under Grant No. 2611120123004 awarded by the Department of Defense Telemedicine and Advanced Technology Research Center (TATRC). Accordingly, the government may have certain rights in the invention.

TECHNICAL FIELD

The present invention relates to various material handling and/or delivery systems and related components, including material handling and/or delivery systems for performing surgical procedures through a natural orifice or a single incision. Certain embodiments include various material handling and/or systems for performing surgical procedures in the peritoneal cavity of a patient.

BACKGROUND

Endoscopic medical procedures have been in use for nearly a century, and are used for a number of procedures such as foreign object removal, ultrasonic imaging, injection therapy, and perhaps most recently for surgical procedures. Endoluminal endoscopic surgery traditionally uses flexible instruments introduced through canals (working channels) in an endoscope to perform a number of procedures, mainly in the peritoneal cavity.

Natural orifice translumenal endoscopic surgery (NOTES) is a surgical procedure done endoscopically through an incision in tissue (e.g., stomach, colon, vagina, or bladder) accessible via a natural orifice (e.g., mouth, anus, urethra, or vagina) and can be done without external incisions, reducing the risk of infection and speeding recovery. The natural orifice access point, while having many patient benefits, presents challenges for introducing instrumentation through a restrictive lumen size, and when using multiple tools, as typical in many laparoscopic procedures for example, tool triangulation can be difficult.

An alternative to traditional endoscope based techniques is using in vivo robots via a natural orifice approach. These in vivo robots can be fully introduced into the peritoneal cavity. Once inserted, these robots have much more freedom and flexibility, as space constraints and tool triangulation issues are greatly reduced in the insufflated abdominal cavity.

Fully inserting in vivo robots into the body introduces a limitation as they are physically isolated from the medical professionals performing the procedure. Without external incisions, there is also a need for additional functional features, such as workspace lighting, a method of irrigating and evacuating fluids produced during procedures, and any other functionalities commonly associated with traditional endoscopic procedures.

There is a need for an improved material handling system for use with surgical procedures.

SUMMARY

One embodiment disclosed herein relates to a system for handling and/or delivering materials during endoscopic surgery, the system including a compliant overtube, a material capture device, and a drive member.

In one embodiment, a system provided herein is configured to transport a material between the outside of an endoscopic surgery patient and the inside of the endoscopic surgery patient, the system comprising a compliant overtube having a primary lumen and a proximal end and a distal end; a material capture device including a retaining mechanism disposed within the primary lumen; and a drive member configured to shuttle the material capture device between the proximal end and the distal end. The drive member can be a helical drive member disposed within the primary lumen. The capture device can further include a tab that can be disposed between adjoining coils of the helical drive member and the slot further can be disposed into a slot defined in the wall of the primary lumen. The slot can constrain the orientation of the material capture device within the primary lumen.

In another embodiment, the system can have a drive member that is a hydraulic or pneumatic system.

In some embodiments, the retaining mechanism comprises a passive spring-type grasper, which, in some embodiments, can comprise a shape memory alloy. A passive spring-type grasper retaining mechanism can be shaped into a plateau-like profile.

In some embodiments, the system can include a motor that drives the drive member housed within an electronic housing. Motor controls can be disposed on or within the electronic housing, or the motor can be controlled using components remote from the electronic housing.

In some embodiments, the system is configured for use in transgastric endoscopic surgery.

In some embodiments, the system includes a compliant overtube comprising silicone.

In one embodiment, a method for transporting a material between the outside of an endoscopic surgery patient and the inside of the endoscopic surgery patient is provided. The method comprises inserting through an incision in the endoscopic surgery patient a distal end of a compliant overtube having: a primary lumen; a material capture device comprising a retaining mechanism disposed within the primary lumen; and a drive member configured to shuttle the material capture device between the proximal end and the distal end. The method further comprises retaining the material in the retaining mechanism of the material capture device and actuating the drive member to advance the material capture device and the retained material from the inside of the patient to the outside of the patient or from the outside of the patient to the inside of the patient. The drive member can be a helical drive member disposed within the primary lumen, or the drive member can be a hydraulic or pneumatic system.

In some embodiments, the distal end of the compliant overtube is inserted through an incision that is in a tissue that is accessible through a natural orifice.

In some embodiments, the retaining mechanism comprises a passive spring-type grasper, which, in some embodiments, can comprise a shape memory alloy.

While multiple embodiments are disclosed, still other embodiments of the present invention will become apparent to those skilled in the art from the following detailed description, which shows and describes illustrative embodiments of the invention.

Accordingly, the drawings and detailed description are to be regarded as illustrative in nature and not restrictive.

It is to be understood that the figures are illustrated for simplicity and clarity and are not necessarily drawn to scale. For example, the dimensions of some of the elements in the figures may be exaggerated, relative to other elements, to improve the understanding of aspects and sample embodiments of the invention.

DETAILED DESCRIPTION

The various systems and devices disclosed herein relate to devices for use in medical procedures and systems. More specifically, the various embodiments relate to systems that can be used to handle and/or deliver materials in endoscopic surgery, such as natural orifice translumenal endoscopic surgery (NOTES). Various embodiments of the disclosed systems and devices can be used to handle and/or deliver or transport one or more materials between the outside of an endoscopic surgery patient and the inside of the endoscopic surgery patient. In some embodiments, the provided systems improve the ability of a medical professional to perform surgical procedures in the peritoneal cavity of a patient, executed through a natural orifice or other access point in conjunction with other surgical equipment.

Figure 1:
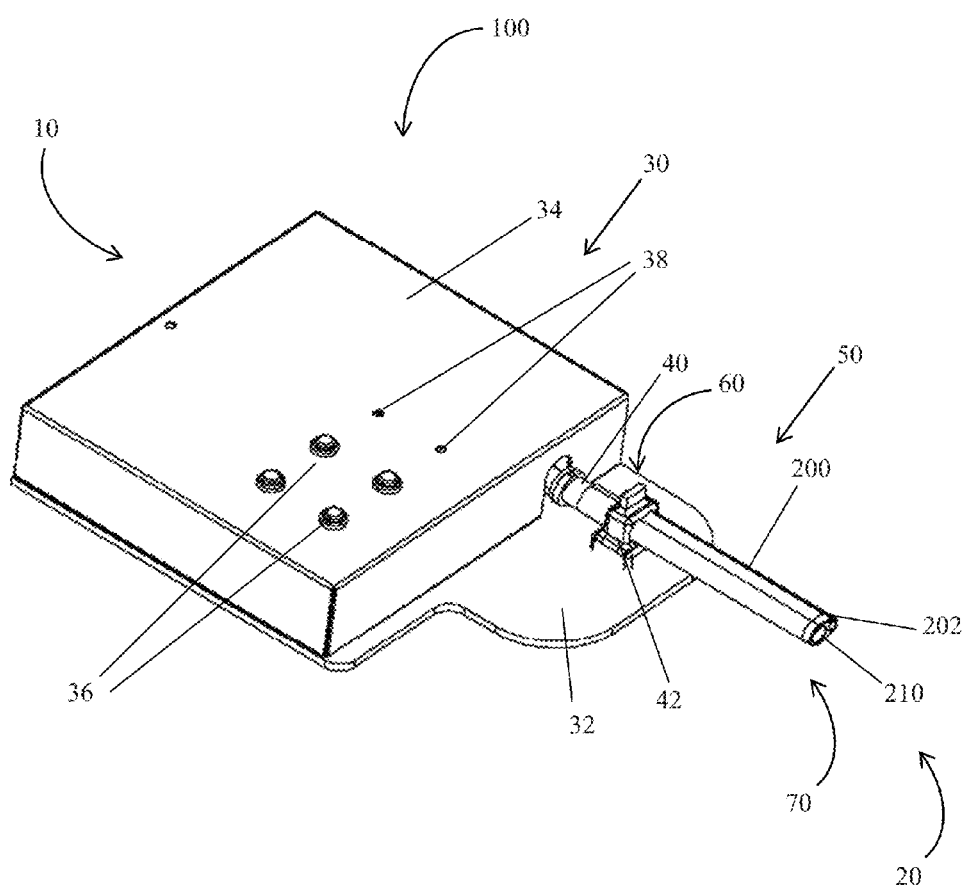
FIG. 1 is an isometric view of the material handling system, according to one embodiment.

Certain embodiments disclosed herein relate to devices for use in endoscopic surgery, including certain embodiments for use in natural orifice translumenal endoscopic surgery (NOTES). FIG. 1 depicts one embodiment of a material handling and/or delivery system 100 having a proximal end 10 and a distal end 20. In the material handling system 100 depicted in FIG. 1, the system includes an electronics housing 30 and a material handling component 50.

Figure 2:
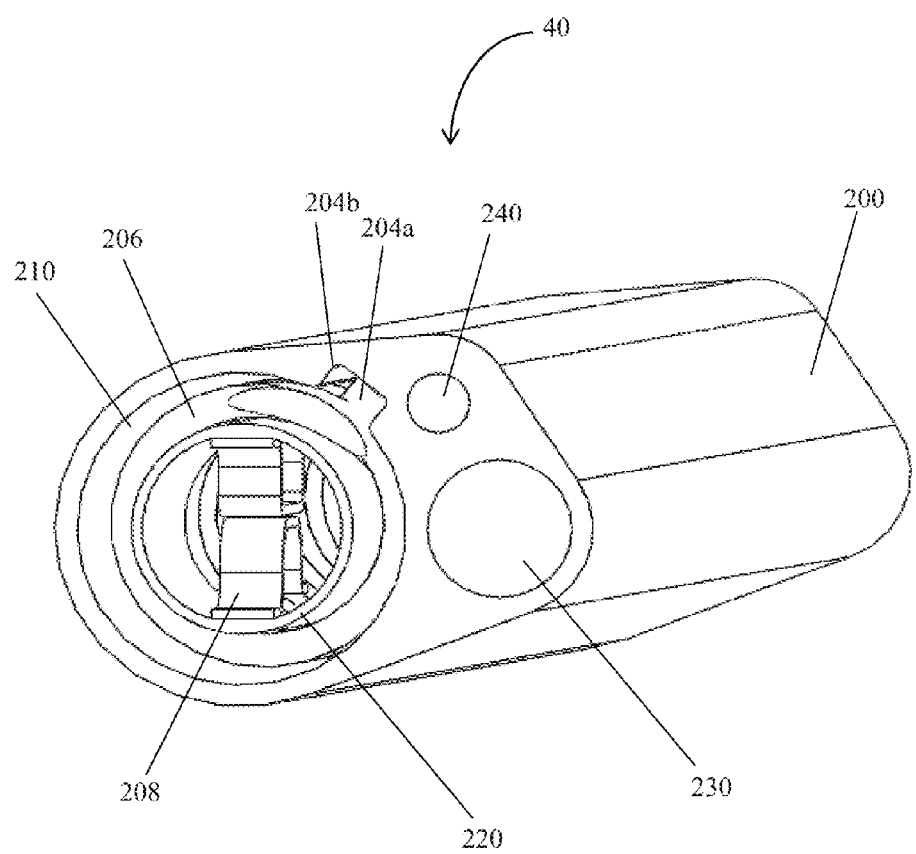
FIG. 2 is a cross sectional view of a distal portion of a material handling system, according to one embodiment.

As best shown in FIGS. 1 and 2, the material handling component 50 comprises a compliant overtube 200 having a proximal end 60 and a distal end 70 and including a primary lumen 210 disposed therethrough. In some embodiments, one or more additional lumens 230, 240 are also disposed within and along the length of overtube 200, as best shown in FIG. 2. The compliant overtube 200 comprises one or more materials that impart flexibility and frictional properties that are conducive to abrasion resistance, while reducing the amount of trauma caused to a patient by the overtube 200 during a surgical procedure. In one embodiment, the overtube 200 is capable of bending to the contours of a natural orifice, such as the esophagus, as well as the peritoneal cavity.

Materials suitable for use in the overtube 200 include, for example, silicone, PTFE, or vinyl. The type of material selected for use in the overtube 200 may depend on the specific use. For example, silicone may be used in an overtube 200 for use in transgastric NOTES in order to provide sufficient flexibility along the length of the esophagus. In addition, in some embodiments, the properties of the material used for the overtube 200 may be modified using known techniques to provide the desired flexibility, frictional properties, and/or abrasion resistance. For example, the coefficient of friction of materials (e.g., silicone and other rubbery materials) can be decreased by the addition of wet and/or dry lubricants, or permanently bonded coatings.

Overtube 200 is shaped and dimensioned as appropriate for the desired use. For example, an overtube 200 for use in transgastric NOTES can have an outer surface of any shape to accommodate the primary lumen 210 and any other lumens, so long as the overall diameter allows the overtube 200 to traverse an esophagus having an average bend radius of about 7.5 cm.

Figure 3:
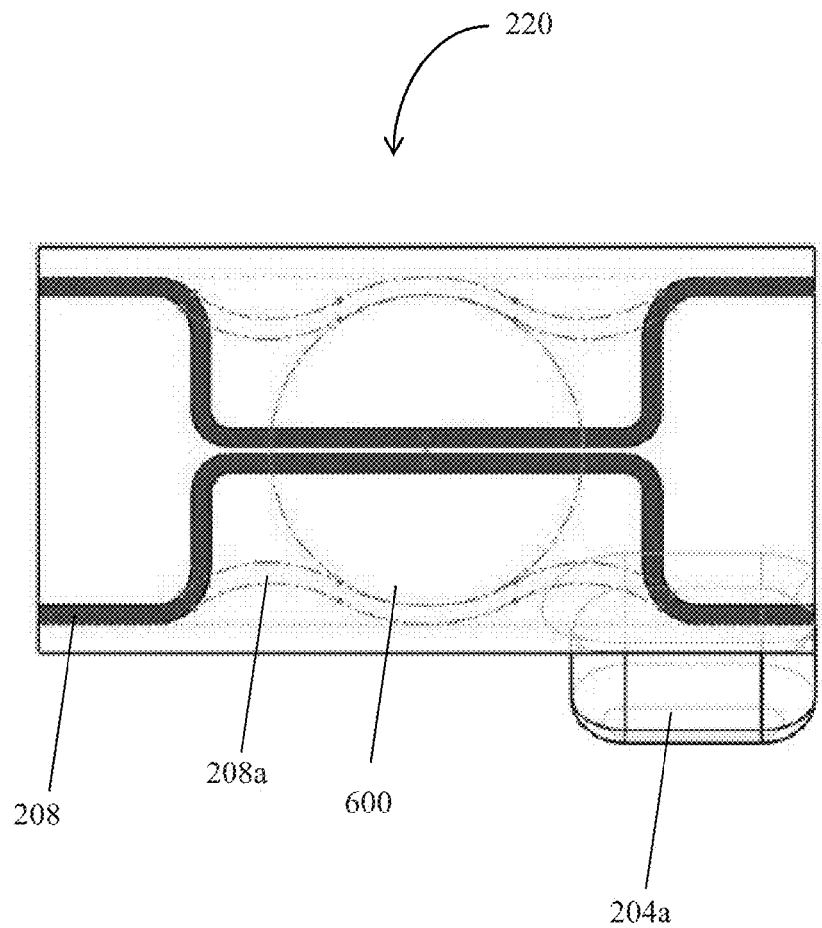
FIG. 3 is a side view of a material capture device of a material handling system, according to one embodiment.
Figure 4:
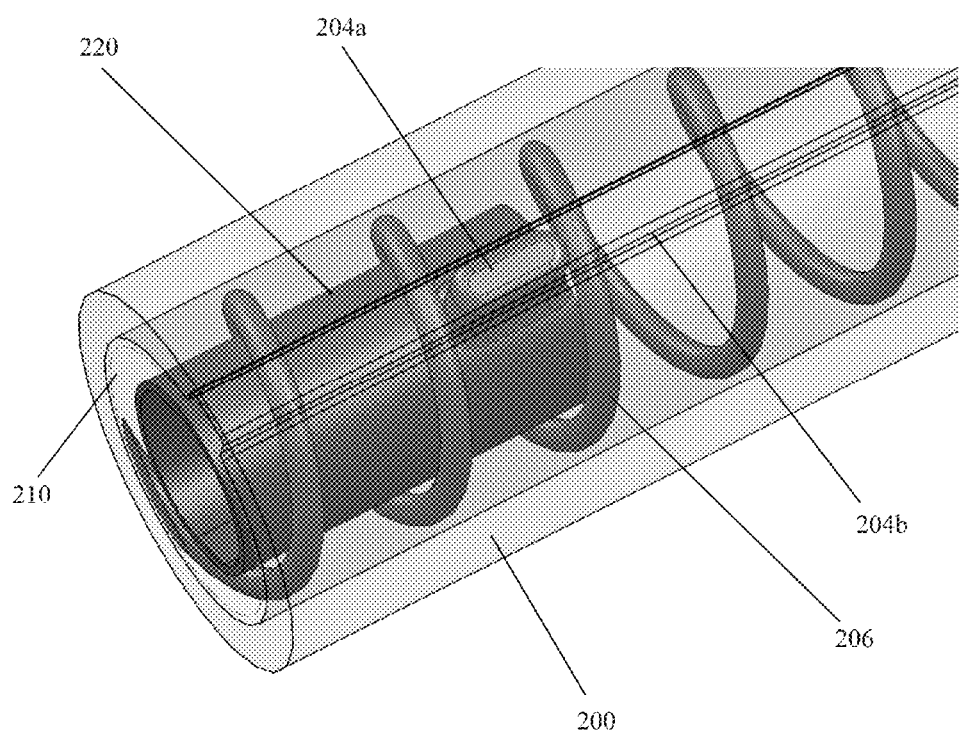
FIG. 4 is a view of a portion of a material handling system with the exterior shown transparently to reveal inner components, according to one embodiment.

As best shown in FIGS. 2-4, in one embodiment, a material capture device 220 is slidably housed within the primary lumen 210 of the overtube 200. A retaining mechanism 208 is coupled with the material capture device 220 to releasably secure one or more materials (e.g., sutures, excised tissue, tool tips, waste bags, diagnostic sensors, or the like) to the material capture device 220. As best shown in FIG. 3, in one embodiment, the retaining mechanism 208 is a passive spring-type grasper comprising, for example a shape memory alloy (e.g., nickel-titanium, copper-zinc-aluminum-nickel, or copper-aluminum-nickel). In this embodiment, the retaining mechanism 208 is a thin ribbon of super-elastic shape memory alloy shaped into a plateau-like profile in its resting state (shown as dark heavy lines in FIG. 3). The spring-type grasper retaining mechanism 208 shown in FIG. 3 deforms (shown in light lines 208a) to accommodate the insertion of a material 600. In some embodiments, the retaining mechanism 208 can comprise a plurality of passive spring-type graspers and/or an alternative passive spring-type grasper configuration, such as a multipronged grasper (e.g., 3- or 4-pronged grasper; not shown). Alternatively, the retaining mechanism 208 can be an actively actuated grasper, such as in a hinged jaw configuration (not shown). In some embodiments, the retaining mechanism 208 is actuated using a linear, rotary, hydraulic, or pneumatic actuator (not shown).

Material capture device 220 and retaining mechanism 208 are configured such that, as the material capture device 220 slides between the proximal and distal ends 60, 70 of the compliant overtube 200, the one or more materials are transported between the proximal and distal ends 60, 70 of compliant overtube 200. The material capture device 220 is dimensioned and shaped as appropriate to accommodate a desired retaining mechanism 208 and to allow access to the retaining mechanism 208 at both the proximal 60 and distal 70 ends of the compliant overtube. In the embodiment shown in FIG. 3, the material capture device 220 is shaped as a hollow section of tube within which a retaining mechanism 208 can be inserted and affixed.

Figure 5A:
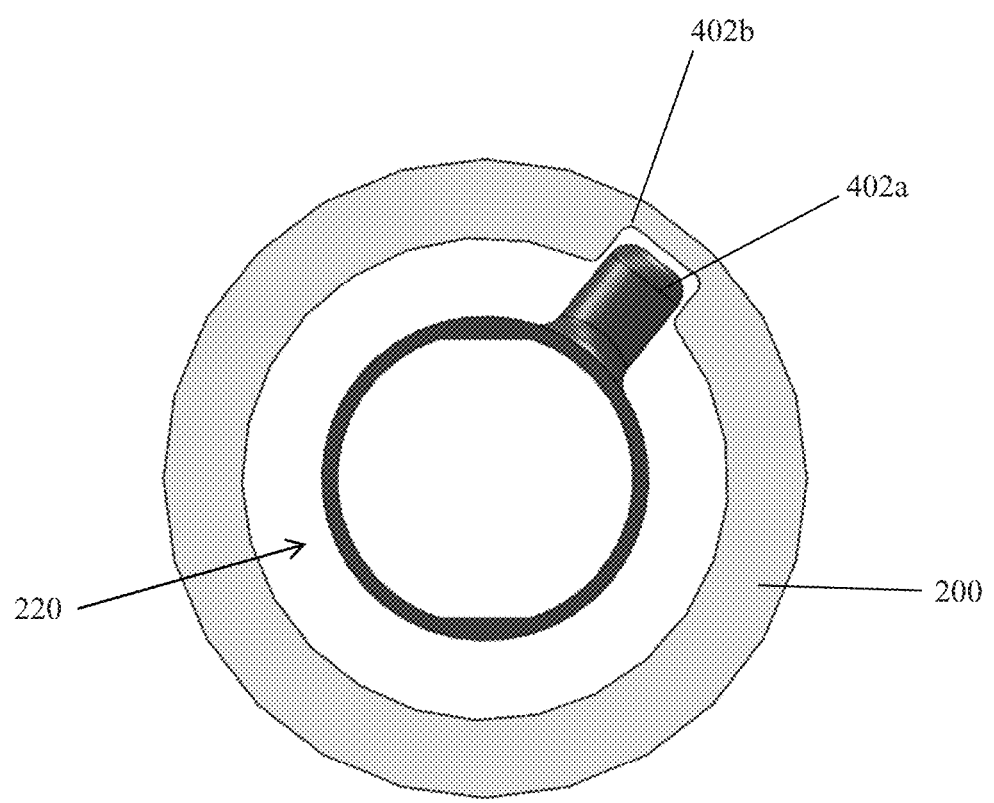
FIG. 5A is a cross sectional view of a material capture device orientation mechanism for a material handling system, according to one embodiment.

As best shown in FIG. 4, a rotating helical drive member 206 is disposed within the primary lumen 210 of compliant overtube 200. In one embodiment, as best shown in FIGS. 4 and 5A, the material capture device 220 is dimensioned to fit within drive member 206 and is operably associated with the drive member 206 via an attached tab 204a that can be disposed between adjoining coils of the helical drive member 206. Slot 204b defined in the wall of primary lumen 210 constrains the orientation of tab 204a, and thereby the orientation of material capture device 220, such that rotation of drive member 206 causes translation of the material capture device 220 axially along the compliant overtube 200.

Figure 5B:
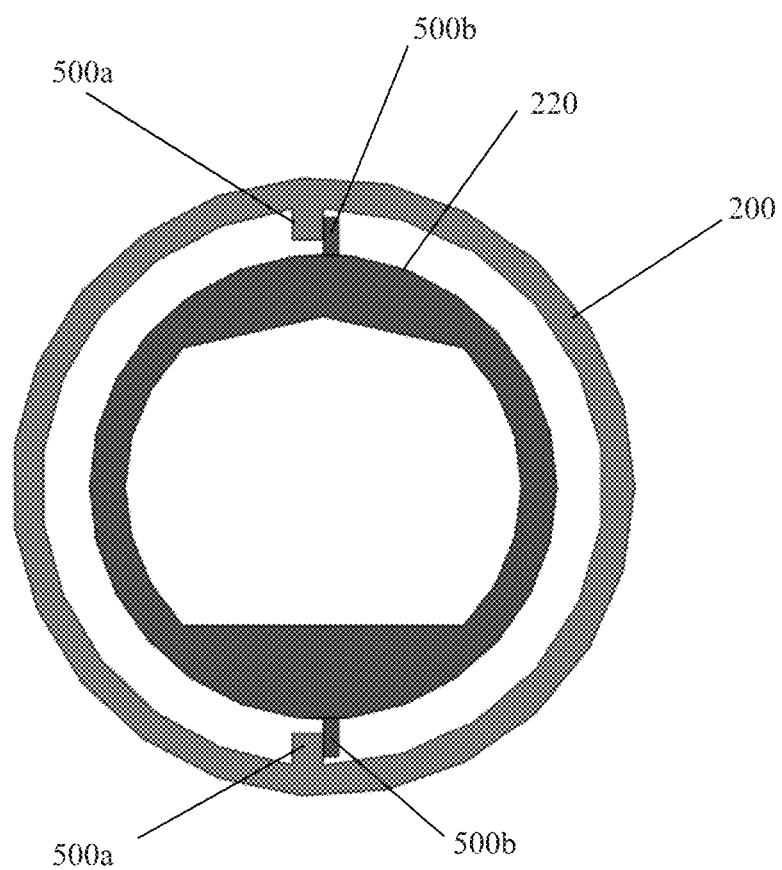
FIG. 5B is a cross sectional view of a material capture device orientation mechanism for a material handling system, according to another embodiment.

Alternatively, as best shown in FIG. 5B, the overtube 200 comprises offset tabs 500a disposed along the length of the interior of primary lumen 210 and material capture device 220 comprises shuttle tabs 500b to orient the material capture device 220 with respect to the compliant overtube 200.

In a further alternative, the material capture device 220 can have any known structure for allowing the device 220 to be urged along the length of the overtube 200.

Figure 6:
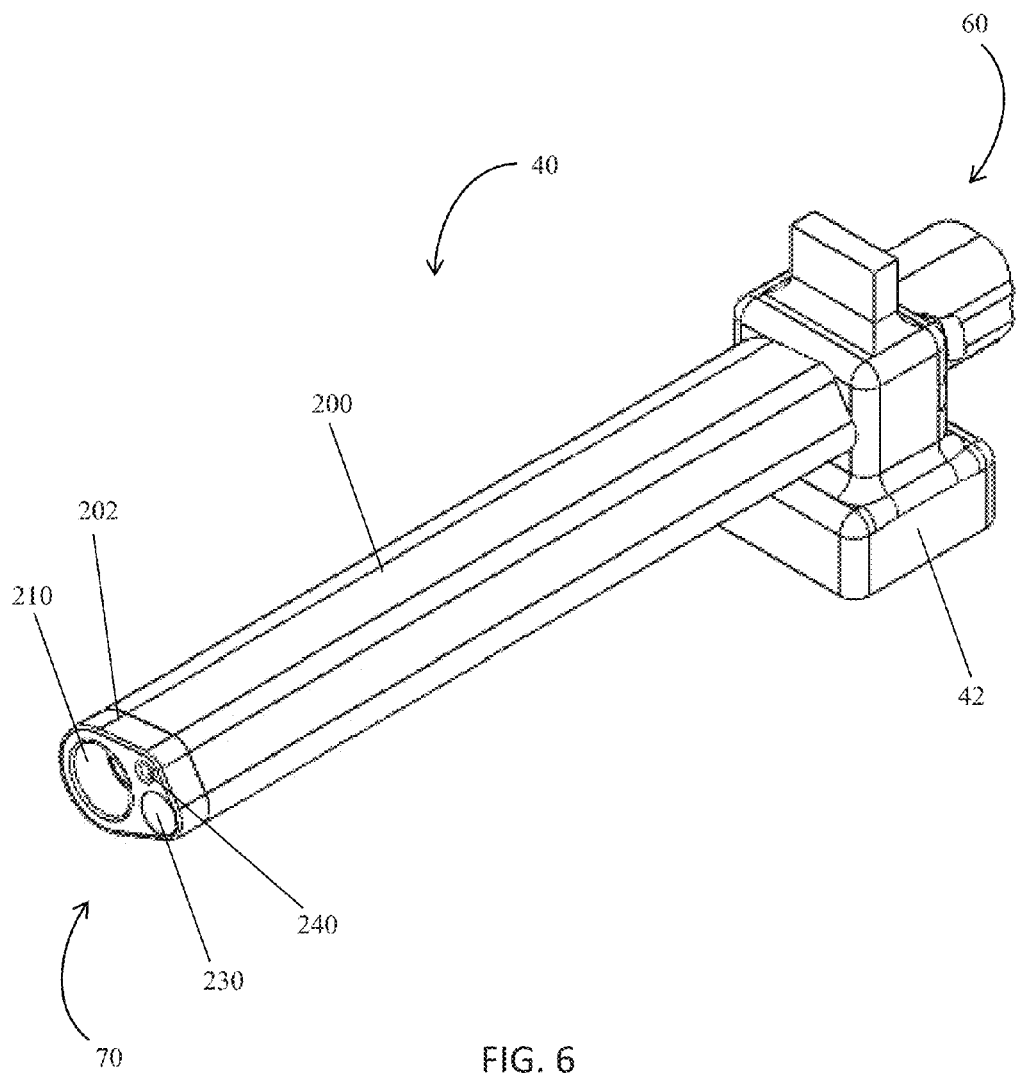
FIG. 6 is a perspective view of a distal portion of the material handling system, according to one embodiment.

As best shown in FIGS. 1 and 6, the drive member 206 of FIG. 4 is retained within the compliant overtube 200 by an overtube cap 202 on the distal end 70 of compliant overtube 200 and with an overtube coupling 42 on the proximal end 60. In one embodiment the overtube cap 202 is configured to provide an access point to interface with other surgical equipment (not shown), such as an in vivo robot, while minimizing the overall diameter of the end of the material delivery system 100 that may be inserted into a patient, thus reducing procedural trauma on surrounding tissues. In some embodiments, the overtube cap 202 is configured to retain the drive member 206 while allowing medical professionals to access the material capture device 220. In another embodiment, the overtube coupling 42 is configured to provide access to the material capture device 220 and provide a location to couple the compliant overtube 200 to the rest of the material handling system 100.

Figure 7:
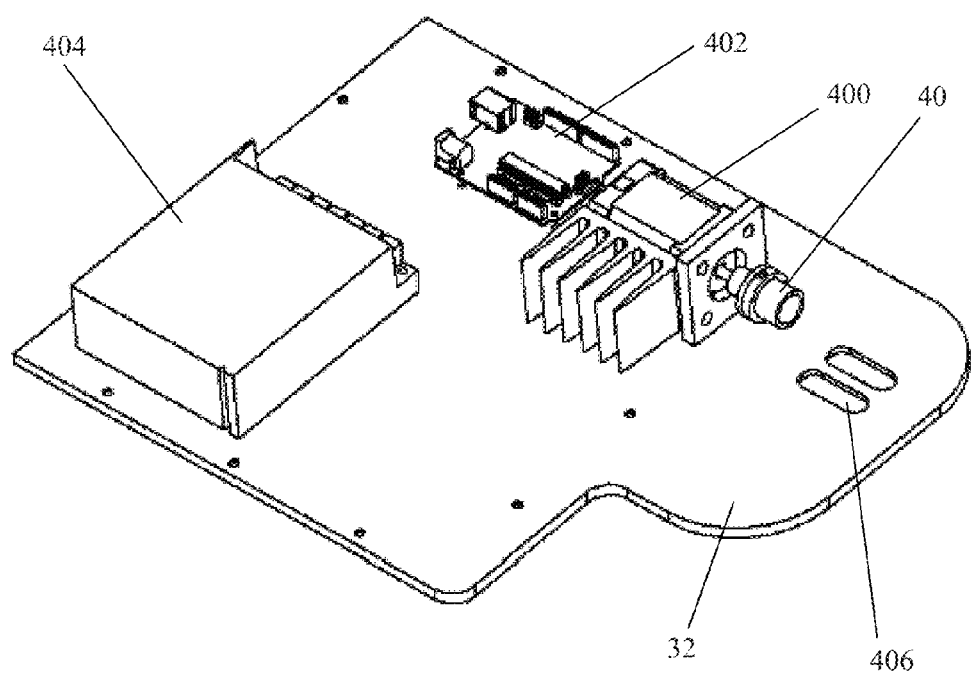
FIG. 7 is a top view of a motor assembly, a micro-control unit, and a power source for a material handling system, according to one embodiment.

As best shown in FIGS. 1 and 7, drive member 206 of FIG. 4 is coupled to motor 400 via a motor coupling 40. The drive member 206 can be releasably coupled to the motor coupling 40, such that the material handling component 50 is detachable from the electronic housing 30. The motor coupling 40 can be a two-piece design, with one half rigidly attached to the motor 400, and the other rigidly attached to the drive member 206, allowing for detachment of the drive member 206 from the motor 400 such that a medical professional can access the material capture device 220. To ensure proper alignment of the compliant overtube 200 and drive member 206 to the motor 400, an overtube coupling 42 as shown in FIG. 1 can be attached near the proximal end of the overtube 200 and coupled to the base plate 32 via an overtube mount 406 located on the base plate 32 (FIG. 7). In one embodiment, the overtube mount 406 may utilize permanent magnets, embedded both in the base plate 32 and in the overtube coupling 42, enabling positive coupling and quick removal and re-attachment of the material handling component 50 to the electronic housing 30 when a medical professional accesses the material capture device 220.

In another embodiment (not shown), the drive member may be a hydraulic or pneumatic system where a secondary lumen 230 or tertiary lumen 240 as shown in FIG. 2 may be used as a hydraulic or pneumatic channel to drive the material capture device 220. In this embodiment, the motor 400 may be substituted with a hydraulic or pneumatic apparatus.

Continuing with FIGS. 1 and 7, in some embodiments, the motor 400 is housed in an electronic housing 30 comprising a baseplate 32 and a top plate 34 that are removably attached to one another. In some embodiments, the motor 400 is attached to the baseplate 32 and/or the top plate 34. The electronic housing 30 can house additional components such as a micro-control unit 402 and/or a power supply 404 for motor 400.

The micro-control unit 402 and/or the power supply 404 can be attached to the base plate 32 and/or top plate 34 similarly to the motor 400. The top plate 34 and base plate 32 can be made of materials suitable for protecting electronic components from damage. In some embodiments, the base plate 32 and/or top plate 34 may be omitted from the material handling system 100.

In one embodiment, as best shown in FIG. 1, the top plate supports operational controls 36. Operational controls 36 can include, for example, momentary contact pushbuttons for automatic and/or manual control of the motor 400, which would propel the drive member 206. Alternatively, operational controls 36 can be located on a separate component (e.g., a computer) that is in electronic communication with one or more components housed in the electronic housing 30.

In one embodiment, the motor 400 may operate using an open-loop logic from a micro-control unit 402. The motor speed and the number of coils per unit length of the drive member 206 can be adjusted to control the rate of speed at which the material capture device 220 traverses the length of the overtube 200. For example, a rotation rate of 650 rpm with a drive member 206 having 3 coils per inch will allow the material capture device 220 to traverse an overtube 200 with a length of about 1 meter in 10 seconds. The motor speed and number of coils per unit length of the drive member 206 can additionally be adjusted to control the level of friction between the material capture device 220 and the drive member 206 and/or the overtube 200.

The micro-control unit 402 can include a motor position sensor (not shown) that can be used to calculate the position of the material capture device 220 within compliant overtube 200 based on the rotation count of the motor 400 and the coil configuration of the drive member 206. In one embodiment, as best shown in FIG. 1, the top plate houses one or more location indicators 38 that can be used to display the position of the material capture device 220 within compliant overtube 200.

The provided material handling system 100 can be used to provide the bridge between other surgical instrumentation, such as in vivo robots, and medical professionals. To facilitate this function, the compliant overtube 200 may contain a secondary lumen 230 and/or a tertiary lumen 240, as best shown in FIG. 2. These lumens may provide additional functionality for a medical professional, for example a lighting port, a video port and/or a port for suction and/or irrigation. In one embodiment, the secondary lumen 230 allows for insertion of a flexible fiberscope that has integrated lighting and video capabilities, and the tertiary lumen 240 has the structural integrity to sustain pressures from a suction/irrigation pump. Further lumens may also be provided.

In use, the material handling system 100 may be inserted into a person by a medical professional in a number of ways. In one embodiment, the compliant overtube 200 and the components located within may be passed through a natural orifice without active steering, relying only on the compliance in the system to guide the device into the peritoneal cavity. In another embodiment, an articulated fiberscope may be inserted into a secondary lumen 230, after which the compliant overtube 200 and the components located within may be passed through a natural orifice, as a medical professional actively steers the device with the articulated fiberscope. In yet another embodiment, the drive member 206, material capture device 200, and overtube coupling 42 may be removed from the compliant overtube 200, an articulated endoscope may be inserted into the lumen 210 where the removed components were located, after which the compliant overtube 200 may be passed through a natural orifice, as a medical professional actively steers the device using the articulated endoscope. The endoscope would then be removed, and the drive member 206, material capture device 220, and overtube coupling 42 may be reinstalled on the compliant overtube 200.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The invention claimed is:

1. A system configured to transport a material between the outside and the inside of a patient undergoing laparoscopic surgery and an insufflated abdominal cavity, the system comprising:
   a. a compliant overtube further comprising at least a primary lumen and a proximal end and a distal end;
   b. a material capture device comprising a retaining mechanism disposed within the primary lumen; and
   c. a helical drive member disposed within the primary lumen and configured to repeatedly shuttle the material capture device between the proximal end and the distal end and into the insufflated abdominal cavity of the patient,
      wherein the material capture device further comprises a tab that can be disposed between adjoining coils of the helical drive member and further can be disposed into a slot defined in the wall of the primary lumen, wherein the slot constrains the orientation of the material capture device within the primary lumen.

2. The system of claim 1, wherein the retaining mechanism comprises a passive spring-type grasper.

3. The system of claim 2, wherein the retaining mechanism comprises a shape memory alloy.

4. The system of claim 2, wherein the retaining mechanism is shaped into a plateau-like profile.

5. The system of claim 1, wherein a motor that drives the drive member is housed within an electronic housing.

6. The system of claim 5, further comprising motor controls disposed on or within the electronic housing.

7. The system of claim 5, wherein the motor is controlled using components remote from the electronic housing.

8. The system of claim 1, wherein the compliant overtube comprises silicone.

9. The system of claim 1, further comprising at least a secondary lumen.

10. The system of claim 9, wherein the at least secondary lumen is capable of providing at least one port selected from the group consisting of: a lighting port, a video port, a suction and an irrigation port.

11. A method for transporting a material between the outside and the inside of a natural orifice translumenal endoscopic surgery patient having an insufflated abdomen, comprising:
   a. inserting through an incision in the natural orifice translumenal endoscopic surgery patient a distal end of a compliant overtube having:
      i. a primary lumen;
      ii. a material capture device comprising a retaining mechanism disposed within the primary lumen wherein the retaining mechanism further comprises a passive spring-type grasper and a shape memory alloy; and
      iii. a drive member configured to repeatedly shuttle the material capture device between the proximal end and the distal end;
   b. retaining the material in the retaining mechanism of the material capture device; and
   c. actuating the drive member to advance the material capture device and the retained material from the insufflated abdomen of the patient to the outside of the patient or from the outside of the patient to the insufflated abdomen of the patient.

12. The method of claim 11, wherein the incision is in a tissue that is accessible through a natural orifice.

13. The method of claim 11, wherein the drive member is a helical drive member disposed within the primary lumen.

14. The method of claim 11, wherein the drive member is a hydraulic or pneumatic system.

15. The method of claim 11, wherein the material is selected from the group consisting of: sutures, excised tissue, tool tips, waste bags, and diagnostic sensors.

16. The method of claim 11, further comprising at least a secondary lumen.

17. The method of claim 15, wherein the at least secondary lumen is capable of providing at least one port selected from the group consisting of: a lighting port, a video port, a suction and an irrigation port.

18. The method of claim 11, wherein the material is selected from the group consisting of: sutures, excised tissue, tool tips, waste bags, and diagnostic sensors.

* * * * *